United States Patent [19]

Li

[11] Patent Number: 4,822,923

[45] Date of Patent: Apr. 18, 1989

[54] ISOMERIZATION OF BY-PRODUCTS OF BIS-PHENOL SYNTHESIS

[75] Inventor: Simon M. Li, Houston, Tex.

[73] Assignee: Shell Oil Company, Houston, Tex.

[21] Appl. No.: 111,240

[22] Filed: Oct. 19, 1987

[51] Int. Cl.[4] .................. C07C 37/68; C07C 39/16
[52] U.S. Cl. ............................ 568/724; 568/722; 568/723; 568/727; 568/728
[58] Field of Search ............... 568/722, 723, 724, 727, 568/728

[56] References Cited

U.S. PATENT DOCUMENTS

| | | | |
|---|---|---|---|
| 2,730,552 | 1/1956 | Williamson | 260/619 |
| 3,221,061 | 11/1965 | Grover et al. | 260/619 |
| 4,375,567 | 3/1983 | Faler | 568/727 |
| 4,400,555 | 8/1983 | Mendiratta | 568/728 |
| 4,590,303 | 5/1986 | Mendiratta | 568/728 |

FOREIGN PATENT DOCUMENTS 1185102 3/1970 United Kingdom.

Primary Examiner—Werren B. Lone

[57] ABSTRACT

By-products of bis-phenol synthesis are isomerized in the presence of an acid catalyst and a free mercaptan co-catalyst.

22 Claims, 1 Drawing Sheet

ISOMERIZATION OF BY-PRODUCTS OF BIS-PHENOL SYNTHESIS

FIELD OF THE INVENTION

The present invention relates to the isomerization of by-products from the preparation of a bis-phenol.

BACKGROUND OF THE INVENTION

Many processes are known to prepare bis-phenol-A. In some of these processes phenol is reacted with acetone to form bis-phenol-A. It is customary to then isolate the bis-phenol-A by crystallization, distillation or adduct crystallization. The concentrated residue contains many isomerizable components, such as o,p'-bis-phenol-A and other variations from bis-phenol-A. These components of the residue are usually isomerized in an acidic medium to the desired bis-phenol-A. The acidic medium includes inorganic acids such as hydrochloric acid and acidic cation exchange resins.

U.S. Pat. No. 3,221,061 discloses the preparation of bis-phenol-A and a subsequent "rearrangement" reaction conducted in the presence of a phenol saturated (mercapto alcohol modified) cation exchange resin.

U.S. Pat. No. 4,400,555 discloses a multi-step sythesis in which acetone is injected in portions and an isomerization follows but the patent fails to illustrate the kind of catalyst in the isomerization zone.

U.S. Pat. No. 4,590,303 discloses a similar process in which the catalyst in the "rearrangement" reaction is a mercapto modified macroporous ion exchange resin but again the acetone is injected into the "rearrangement" reactor and while the total conversion of acetone was increased, the percentage of undesired by-products also increased. However, from the data in the experiments in this patent, it can be seen that diverting a part of the acetone to the "rearrangement" reactor was adverse to isomerization since the selectivity to the desired bis-phenol-A became progressively worse. Thus, the desired isomerization was not demonstrated.

U.S. Pat. No. 4,375,567 discloses that both microreticular and macroreticular ion exchange resins in an unmodified form are used for isomerization. In this case, the microreticular resins were less effective for isomerization than the macroreticular resins.

U.S. Pat. No. 2,730,552 discloses the use of an acidic catalyst for the preparation of bis-phenols in the presence of methyl mercaptan but that other alkyl mercaptans are not as effective for promotion in condensation of bis-phenols.

Canadian Pat. No. 859,204 discloses the use of a mercaptan promoter with a cationic ion exchange resin for the condensation of a ketone with a phenol.

There still exists a need to reduce or utilize the amount of undesirable by-products from the preparation of, e.g., bis-phenol-A, from phenol and acetone. Obviously, the art has failed to find a method to react the two starting materials without the production of by-product isomers. Thus, there is still a need to more effectively convert these undesired isomers into the desired bis-phenol. The present invention addresses this problem and provides a new method to isomerize the undesired by-products to the desired bis-phenol.

SUMMARY OF THE INVENTION

The present invention is directed to a process for isomerizing the undesirable dihydroxy isomer containing by-products from the preparation of a bis-phenol in the desired 4,4'-dihydroxy form from a phenol and a ketone, which comprises treating the by-products from the preparation of bis-phenol from the condensation of a ketone and phenol with a catalytic amount of an acid, such as acidic cation exchange resin, in the presence of a free mercaptan co-catalyst to isomerize the by-products and recovering an isomerization product having a higher concentration of the desired bis-phenol having the 4,4'-dihydroxy form.

The present invention is useful in recovering more of a desired bis-phenol, e.g., bis-phenol-A, by isomerization of an undesired bis-phenol such as 2,4'-dihydroxy-2,2-diphenyl propane (commonly referred to as o,p'-BPA) and related by-products to the desired bis-phenol-A with less formation of certain other undesirable impurities such as 1,3,3-trimethyl-p-hydroxy-phenyl-6-hydroxyindane, 4-methyl-2,4-bis-(4'-hydroxyphenyl)pentene-2 and the like.

The present invention is useful for the isomerization of certain undesirable by-products from the preparation of a bis-phenol from a ketone and a phenol. The bis-phenols include those prepared by the reaction of a ketone, such as acetone, ethyl methyl ketone, isobutyl methyl ketone, acetophenone, cyclohexanone, 1,3-dichloroacetone and the like, with a phenol, such as phenol, o-cresol, m-cresol, o-chlorophenol, m-chlorophenol, o-t-butylphenol, 2,5-xylenol, 2,5-di-t-butylphenol o-phenylphenol and the like. The above is not meant to limit the invention but to illustrate representative examples of ketones and phenols which are known in the art to make desirable bis-phenol and for which those of skill in the art can substitute other conventional bis-phenol reactants.

In the preparation of the bis-phenols, an excess of the phenol is usually desirable, generally from about 5 to about 20 moles of phenol per mole of ketone, is desirable for high conversion of the ketone. Solvents or diluents are not necessary in either the preparation of the bis-phenol or in the isomerization of the undesired by-product except at low temperature.

Any conventional acid which functions to isomerize undesired bis-phenol by-products to the desired bis-phenols can be used. These include both inorganic and organic acids or acidic acting materials, for example: mineral acids, such as hydrochloric acid, hydrobromic acid, phosphoric acid, sulfuric acid or the like, sulfonic acids such as toluene sulfonic acid and the like, organic acids such as lower alkanoic acids having from 1 to about 10 carbon atoms, including acetic, propionic, butyric and the like, acidic clays, boron trifluoride complexes, various acidic resins and the like. The acid can be one formed by the hydrolysis with water of compounds such as aluminum chloride, sulfonyl chloride, phosgene and the like. The acid can be a liquid or a solid but is preferably a solid itself or a solid used to carry or support acidic materials.

The catalysts for the isomerization are preferably acidic cation exchange resins. Such resins which can be used as catalysts are conventionally known in the art and include those acidic cation exchange resins that are unmodified with a mercapto modifying agent before use in the isomerization process, but which are used with the addition of a free mercaptan co-catalyst to the isomerization process.

The resin is essentially not modified to any substantial degree with the free mercaptan. The free mercaptan can be any free mercaptan of the type conventionally known in the art which includes any compound which will not react substantially under the isomerization conditions with the acid catalyst, including mercaptans, will not react with the acidic groups of the cation exchange resin to introduce a mercaptan substituent into the resin. Suitable mercaptan co-catalyst include those of the formula RSH in which R is hydrogen or an organic group such as aliphatic, cycloaliphatic, aryl or heterocyclic compounds containing one or more free mercaptan groups. For convenience, the mercaptan usually is a non-resinous compound containing from about 1-20 carbon atoms. Simple alkyl mercaptans, mercapto acids and precursors and the like, for example, methyl mercaptan, dithioethane, ethyl mercaptan, n-pentyl mercaptan, thioglycolic acid, 1,2-dimercapto ethane, and the like. Alkyl mercaptans are preferred, especially methyl mercaptan. The amount of mercaptan present can vary with the acid used but is usually present in a lesser amount compared to the acid. For example, the mercaptan is present from about 1 mole percent to about 100 mole percent based on the acid and preferably from about 5 to about 50 moles percent.

The effectiveness of the resin catalysts in the isomerization process of the invention is to some extent influenced by their exchange capacities such that the greater the exchange capacity then the more desirable the resin is for isomerization. Preferably, the cation exchange capacity is at least about 0.5 and, preferably, greater than 4.0 meq/g dry weight. Also, those cation exchange resins having bound cationic exchange groups of the stronger exchange potential acids are preferred for use in the resin and free mercaptan co-catalyst isomerization process of the present invention. Acidic cation exchange resins suitable for use with a free mercaptan co-catalyst in isomerization include sulfonated styrene-divinylbenzene copolymers, sulfonated cross-linked styrene polymers, phenol-formaldehyde-sulfonic acid resins, benzene-formaldehydesulfonic acid resins and the like. These include resins under such tradenames as Amberlites (Rohm and Haas Co.), DOWEX ® (Dow Chemical Co.), Permutit QH (Permutit CO.), CHempro (Chemical Process Co,), Lewatit (Bayer A.G.) and the like. Strong acid sulfonated styrenedivinylbenzene copolymers are preferred. Both modified macroreticular resins and microreticular resins are useful in the isomerization process of the present invention. Macroreticular resins are preferred. The choice of resin will of course depend on the material to be isomerized, the reaction conditions and the effect of an individual resin under the conditions selected, which determination and selection is within the skill of the art. Commercially available aromatic sulfonic acid resins are generally obtained as sodium salts and are converted to the acid from prior to use.

The precise amount of acidic cation exchange resin to be used will vary to some degree depending on the specific resin, feed and conditions used for the isomerization process. By way of illustration, the catalyst can be present from about 0.05 lbs per lb of feed per hour to about 10.0 lbs per lb of feed per hour and, preferably, from 0.2 lbs per about 2 lbs per lb of feed per hour.

The isomerization is usually conducted in the presence of minor amounts of water in the reaction solution of from about 1.5% to essentially anhydrous conditions based on the isomerization reaction solution. Somewhat higher amounts of water can be present but this could result in reduced isomerization efficiency. Somewhat higher amounts of water can also decrease the net formations of the nonreversible impurities in the desired product. Preferably, the water content of the reaction solution is from about 0.1% to about 0.7% based on the isomerization reaction solution.

The isomerization reaction is usually conducted at moderately elevated temperatures. Suitable temperatures are from about 50° C. to about 110° C. at ambient pressure. Preferably, the reaction temperature is from about 60° C. to about 85° C. at ambient pressure.

Thus, the isomerization reaction is conducted by contacting a feed stream containing liquid undesired dihydroxy isomer containing by-products from the preparation of a bis-phenol, such as 2,4'-dihydroxy-2,2-diphenyl propane and related by-products and optionally (phenol) washings from the from the crystallization of bis-phenol-A, with a acidic cationic exchange resin and free mercaptan co-catalyst under moderately elevated temperatures and in the presence of some water. The feed stream passes through the resin catalyst in the presence of free mercaptan for a period of time sufficient to effect isomerization depending on the feed rate, size of the resin bed, the particular resin and co-catalyst used and the like as can readily be determined by those of skill in the art. The resulting isomerization product enriched in the desired bis-phenol having a 4,4'-dihydroxy form, such as bis-phenol-A, is then recovered. Usually the recovered product is recycled back to a zone in which the bis-phenol is prepared by condensation of a ketone (acetone) and phenol.

The reaction time in the isomerization or in the condensation depends on the reaction temperature and other reaction conditions, including whether the process is continuous or batch processing.

Another embodiment of the present invention is directed to a process for the preparation of a bis-phenol having a desired 4,4'-dihydroxy form which comprises (a) condensing a ketone, such as acetone, and a phenol in the presence of an acid catalyst, such as an acidic cation exchange resin, (b) crystallizing an adduct of the phenol and the desired bis-phenol to obtain the desired bis-phenol, and (c) isomerizing the undesired dihydroxy isomer containing by-products of the condensation step (a) optionally with any wash liquids from the crystallization step (b) in the presence of an acid catalyst and a free mercaptan co-catalyst to obtain a product enriched in the desired bis-phenol for recycle to the condensation step (a).

The condensation of acetone and phenol can be conducted using a conventional acid catalyst generally known in the art for the condensation of acetone and phenol. In general, these are often mercapto modified resins of the type described above for use in the isomerization reaction although unmodified resins or acids are most useful because of the free mercaptan recycled from the isomerization zone. A macroreticular resin is preferred. It is a preferred aspect of the present invention that a resin be used for the condensation and be unmodified by mercapto groups because some of the free mercaptan co-catalyst of the isomerization reaction can be readily carried through to the condensation reaction with the recycle isomerization product.

The condensation reaction is conducted at moderately elevated temperature of from about 50° C. to about 130° C. at ambient pressures.

In the preparation of the bis-phenols, an excess of the phenol, generally from about 5 to about 20 moles of phenol per mole of ketone, is desirable for high conversion of the ketone using a cation exchange resin with free mercaptan as a co-catalyst. Solvents or diluents are not necessary in either the preparation of the bis-phenol or in the isomerization of the undesired by-product except at low temperature.

The bis-phenol product, e.g., bis-phenol-A, is passed to a concentrator where the acetone, phenol, and free mercaptan and excess water are removed as an overhead fraction. The crude bis-phenol-A product is then passed to a crystallization zone where it is chilled to about 30° C. to about 95° C. to form an adduct of phenol and bis-phenol-A which separates out as crystals. After washing with phenol, filtering and the like, the bis-phenol-A is recovered from the adduct. The mother liquid by-product stream from the crystallization zone is passed to the isomerization zone, optionally combined with the phenol washings from the crystallization step, and isomerized in the presence of an unmodified acidic cation exchange resin catalyst and a free mercaptan co-catalyst as described above. The product of this isomerization enriched in bis-phenol-A is recovered or preferably recycled with free mercaptan to the condensation zone.

DETAILED DESCRIPTION OF THE DRAWING

Figure 1:
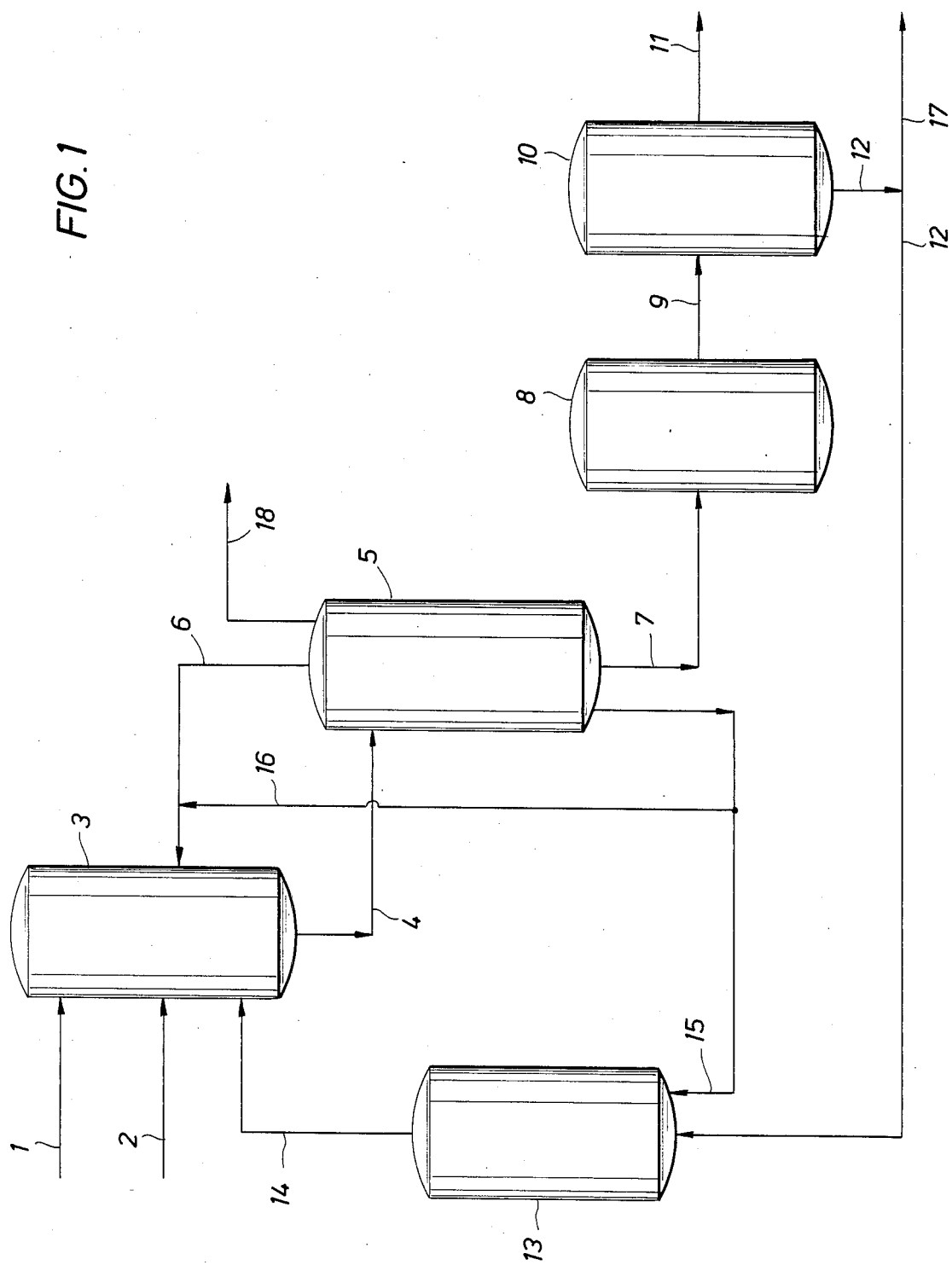
FIG. 1 is a schematic drawing of a process to prepare bis-phenol-A in which acetone and phenol are reacted to form bis-phenol-A and the by-product isomers are subsequently treated in the presence of an unmodified cation exchange resin and free mercaptan in which both the preparation of bis-phenol and the isomerization take place in the presence of unmodified resins and the free mercaptan co-catalyst is preferably injected into the system at the isomerization zone inlet.

With reference to FIG. 1, acetone and phenol reactants are injected into a condensation reactor 3 via lines 1 and 2, respectively, along with any recycle isomerization product added via line 14. Any conventional acid condensation catalyst effective for the formation of bis-phenol-A can be used. However, it is advantageous that the reactor contains an unmodified or modified acidic cation exchange resin, such as a sulfonated polystyrenedivinylbenzene acidic cation exchange resin which does not contain mercapto modifying groups at about 50°–70° C. The reaction product is passed via line 4 into a concentrator 5 in which unreacted acetone and phenol recovered for recycle via line 6 to zone 3. Waste water is removed via line 18. Free mercaptan is removed via line 15 and recylced to the isomerization zone 13 or in part to the condensation zone 3 via line 16 and crude bis-phenol-A product is recovered and passed via line 7 to crystallizer 8 to form a solid bis-phenol-A/phenol adduct. The slurry adduct is passed via line 9 into separator 10 wherein the adduct is separated from the by-product mother liquid and is passed via line 11 into a melter (not shown). The by-product mother liquid is removed from the separator 10 and passed via line 12 into an isomerization zone 13. Line 17 serves as a purge stream. The isomerization zone is maintained at about 60°–90° C. and contains an acidic cationic exchange resin. This is conveniently an unmodified microreticular or macroreticular acidic cation exchange resin which is used in conjunction with a free mercaptan co-catalyst, such as n- pentyl mercaptan, methyl mercaptan, or the like, which is injected via line 15, and includes that free mercaptan recovered from zone 5. The isomerization product, which is increased in concentration of the desired bis-phenol-A and also containing the mercaptan, is recycled to the condensation reactor via line 14.

While the invention has been illustrated with particular apparatus, those of skill in the art will appreciate that equivalent or analogous apparatus or parts thereof can be employed and that the use of equipment operated in series of in parallel can be used. Batch of continuous form can be used. The solid catalysts can be used as a slurry with the reactants in batch processing or in a fixed bed in a continuous process.

ILLUSTRATIVE EMBODIMENT

The invention is illustrated by the following embodiment which should not be regarded as limiting the invention in any way.

EMBODIMENT 1

Experiments were performed in batch at 80° C. using a 1:3 catalyst to reactant weight ratio for the following systems: (1) unmodified macroporous DOWEX MSC-1 and (2) 1% w n-pentyl mercaptan and unmodified macroporous DOWEX MSC-1. Each catalyst was pre-dried in vacuum oven at 60°–70° C. for 1–2 days and the reactant source was by-product from the bis-phenol-A obtained by the condensation of acetone and phenol containing 2,4′-dihydroxy-2,2-diphenyl propane. CDB (1,3,3-trimethyl-p-hydroxyphenyl-6-hydroxyindane), and LDP-1 [4-methyl-2,4-bis-(4′-hydroxyphenyl)pentene-2] are undesirable by-products normally found in the products of isomerization of bis-phenol-A by-products and are also present in the isomerization feed.

Results are given in Table 1 and illustrate that the desired isomerization took place but that less net formation of CDB or LDP-1 and no net formation of heavies or unknowns was obtained by use of the catalyst of the invention.

TABLE 1

Summary of Batch Isomerization of By-products from Bis-phenol-A Synthesis

| System[a] | % w Water[b] | Δ CDB/LDP-1[c] (ppm) | Δ Heavies[c] or unknowns (ppm) |
|---|---|---|---|
| 1 | 0.22 | 5000 | 250 |
|  | 0.35[d] | 1500 | 50 |
| 2 | 0.37 | 500 | — |

[a]System:
1. Unmodified macroporous DOWEX MSC-1.
2. Unmodified macroporous DOWEX MSC-1 with 1% w n-pentyl mercaptan
[b]Water in solution phase.
[c]Net increase at 80° C. after 50% of isomerizable o,p′-BPA has been converted to p,p′-BPA.

What is claimed is:

1. A process for isomerizing the undesired dehydroxy isomer containing by-products from the preparation of a desired bis-phenol having a 4,4′-dihydroxy form which comprises treating the by-products from the preparation of the desired bis-phenol from the condensation of a ketone and a phenol, at about 50° C. to 110° C. and about ambient pressure with a catalytic amount of an acid in the presence of a free mercaptan co-catalyst and a minor amount of water of up to about 1.5 percent weight based on the isomerization reaction solution to isomerize the undesired by-products and recovering a product of a higher concentration of the desired bis-phenol.

2. A process according to claim 1 wherein the co-catalyst is an alkyl mercaptan.

3. A process according to claim 2 wherein the co-catalyst is an alkyl methyl mercaptan or n-pentyl mercaptan.

4. A process according to claim 1 wherein the acid is an acidic cation exchange resin.

5. A process according to claim 4 wherein the resin is selected from sulfonated styrene-divinylbenzene copolymers, sulfonated cross-linked styrene polymers, phenol-formaldehyde-sulfonic acid resins, or benzene-formaldehyde-sulfonic acid resins.

6. A process according to claim 5 wherein the resin is a sulfonated styrene-divinylbenzene copolymer.

7. A process according to claim 6 wherein the resin is a macroreticular resin.

8. A process according to claim 6 wherein the resin is a microreticular resin.

9. A process according to claim 1 wherein the by-products are from the preparation of bis-phenol-A and included undesired 2,4'-dihydroxy-2,2-diphenyl propane.

10. A process according to claim 1 wherein the free mercaptan is an alkyl mercaptan and the acid is an acidic cation exchange resin.

11. A process according to claim 10 wherein methyl mercaptan or n-pentyl mercaptan and a sulfonated styrene-divinylbenzene copolymer are used.

12. A process for the preparation of a bis-phenol which comprises (a) condensing a ketone and a phenol in the presence of an acid catalyst, (b) crystallizing an adduct of the phenol and the desired bis-phenol to obtain the desired bis-phenol, and (c) isomerizing the undesired dehydroxy isomer containing by-products of the condensation step (a) with any phenol wash liquids from the crystallization step (b) at about 50° C. to 110°0 C. and at about ambient pressure in the presence of an acid catalyst and a free mercaptan co-catalyst and a minor amount of water of up to about 1.5% weight based on the isomerization reaction solution to obtain a product enriched in the desired phenol for recycle to the condensation step (a).

13. A process according to claim 12 wherein the co-catalyst is an alkyl mercaptan.

14. A process according to claim 13 wherein the co-catalyst is methyl mercaptan or n-pentyl mercaptan.

15. A process according to claim 14 wherein the resin is selected from sulfonated styrene-divinylbenzene copolymers, sulfonated cross-linked styrene polymers, phenol-formaldehyde-sulfonic acid resins, or benzene-formaldehyde-sulfonic acid resins.

16. A process according to claim 15 wherein the resin is a sulfonated styrene-divinylbenzene.

17. A process according to claim 15 wherein the resin is a macroreticular resin.

18. A process according to claim 15 wherein the resin is a microreticular resin.

19. A process according to claim 12 wherein the resin in the condensation step (a) is initially an unmodified resin.

20. A process according to claim 12 wherein the by-products are from the preparation of bis-phenol-A and included undesired 2,4'-dihydroxy-2,2-diphenyl propane.

21. A process according to claim 20 wherein the free mercaptan is an alkyl mercaptan and the acid is an acidic cation exchange resin.

22. A process according to claim 21 wherein methyl mercaptan or n-pentyl mercaptan and a sulfonated styrene-divinylbenzene copolymer are used.

* * * * *